United States Patent [19]
McPherson et al.

[11] Patent Number: 4,720,543
[45] Date of Patent: Jan. 19, 1988

[54] 1A-7-SUBSTITUTED DERIVATIVES OF MITOMYCIN AND USES THEREOF

[75] Inventors: Eugene McPherson, Forestville, Md.; Philip S. Schein, Bryn Mawr, Pa.

[73] Assignee: Georgetown University, Washington, D.C.

[21] Appl. No.: 742,045

[22] Filed: Jun. 6, 1985

[51] Int. Cl.[4] .................. C07D 487/14; A61K 21/00; A61K 31/40
[52] U.S. Cl. .................................. 536/18.1; 514/908; 536/17.3; 536/17.4; 536/18.7; 536/22; 548/422
[58] Field of Search ..................... 536/17.3, 17.4, 22, 536/18.1; 514/43, 908; 548/422

[56] References Cited

U.S. PATENT DOCUMENTS

| | | | |
|---|---|---|---|
| 3,367,945 | 2/1968 | Matsui et al. | 548/422 |
| 3,450,705 | 6/1969 | Matsui et al. | 260/295 |
| 3,558,651 | 1/1971 | Matsui et al. | 260/326.3 |
| 3,660,578 | 5/1972 | Hata et al. | 424/274 |
| 4,021,449 | 5/1977 | Fujimoto et al. | 260/326.24 |
| 4,268,676 | 5/1981 | Remers et al. | 548/181 |
| 4,395,558 | 7/1983 | Kasai et al. | 548/422 |

FOREIGN PATENT DOCUMENTS

| | | | |
|---|---|---|---|
| 6806627 | 3/1968 | Japan . | |
| 0105583 | 9/1978 | Japan | 536/112 |

OTHER PUBLICATIONS

Oboshi, et al., GANN 58:315-21 (1967). Antitumor Studies on Mitomycin Derivs.II Effect on Solid Tumor of Sarcoma-180.
Usubuchi, et al., GANN58:307-13 (1967). Antitumor Studies on Mitomycin Derivs. I Effect on Hirosaki Ascites Sarcoma.
Matsui, et al., J. Antibiotics 21(3):189-98 (1968). Studies on Mitomycins.III Synth. and Props. of Mitomycin Derivatives.
Cheng, et al., J. Med Chem.20(6):767-70(1977), Compar. Stereochem. in Aziridine Ring Openings of N-Methylmitomycin A and 7-Methoxy-1 2-(N-Methylaziridino) Mitosene.
Iyengar et al., J.Med. Chem. 26:16-20 (1983), Mitomycin C and Porforomycin Analogues with Substituted 7-Ethylamines.
Schein et al., in "Mitomycin C: Current Status and New Developments"; eds., Carter et al., Acad. Press, N.Y., 1979, pp. 133-143.
Sami et al., J. Med. Chem. 27:701-8 (1984), Mitomycin C Analogues with Aryl Substituents on the 7-Amino Group.
Suami et al., J.Med.Chem. 22(3): 247-50 (1979), Synthesis and Activities of Antitumor Agents.
Anderson et al., Cancer Res. 35:761-5 (1975), Chlorozotocin, An Anti-Tumor Agent with Modified Bone Marrow Toxicity.
Panasci et al., J. Clin. Invest.64:1103-11 (1979). Chlorozotocin. Reduced Bone Marrow Toxicity in Mice.
Kinoshita et al., J.Med.Chem. 14(2):103-12 (1971), Mitomycin Derivatives, 1. Prep'n of Mitosane & Mitosene Cpds & Biol. Actions.
Weiss et al., J.Med.Chem., 11:742-6 (1968), Mitomycin Antibiotics, Synthetic Studies, XXII, Antibacterial Structure-Activity Relationships in the Indoloquinone Series.
Patrick et al., J.Amer.Chem.Soc. 86:1889-90 (1964). Aziridinomitosenes: A New Class of Antibiotics Related to the Mitomycins.
Driscoll et al., Cancer Chemotherap. Rep. 4:3-4 (1974). Quinone Structure-Antitumor Activity Relationships.
Kojima et al., Cancer Chemotherap.Rep. 3:111-119 (1972). Influence of Schedule of Admin. of Mitomycin C in Treatment of L1210 Leukemia.

(List continued on next page.)

Primary Examiner—Ronald W. Griffin
Attorney, Agent, or Firm—Steinberg & Raskin

[57] ABSTRACT

This invention discloses 1a- and 7-substituted derivatives of mitosanes containing thiocarbamoyl and glycosyl residues. The compounds possess antibacterial and antitumor activity, with a concomitant reduction in bone marrow toxicity as compared to the parent compounds.

16 Claims, 4 Drawing Figures

OTHER PUBLICATIONS

Goldin et al., NCI-EORTC Sympos. On Mitomycin C, Brussels 1981, pp. 1-17, Preclinical Studies with Mitomycin C and Derivatives.

Kojima et al., Cancer Chemotherap.Reps. 3:121-135 (1972), Some Structure-Activity Relationships for Mitomycin C Derivatives in Treatment of LI2I0 Leukemia.

Kisner et al. Mit.C in Treatment of Gastric and Pancreatic Carcinomas, NCI-EORTC Symp. Mit.C, Brussels, 1981, pp. 64-75.

DeLena et al., Single Agent Activity of Mit.C in Breast Cancer, NCI-EORTC Symp. Mit.C, Brussels, 1981, pp. 89-96.

Israel et al., Mit.C in Nonsmall Cell Lung Cancer, NCI-EORTC Sympos. Mit.C. Brussels. 1981, pp. 106-112.

Godfrey, Mito.C in Breast Cancer, in Mit.C: Current Status and New Developments, Carter et al., eds., Acad. Press, N.Y. 1979, pp. 91-99.

Samson, Clin. Studies of Mit.C in Adv. Adenoarcinoma of the Lung, in Mit.C:, Current Status and New Developments, Carter et al., eds., Acad. Press, N.Y. 1979, pp. 121-127.

1A-7-SUBSTITUTED DERIVATIVES OF MITOMYCIN AND USES THEREOF

BACKGROUND OF THE INVENTION

1. Field of the Invention

This invention is directed to new mitomycin derivatives having good anti-tumor activity while at the same time demonstrating reduced bone marrow toxicity as compared to the parent compounds.

The mitomycin derivatives of the present invention are characterized by thiourea substitution at position 1a and, additionally, glycosyl substitution at either the 1a or 7 position.

2. Brief Description of Related Art

The mitomycins are compounds corresponding to the general formula (I):

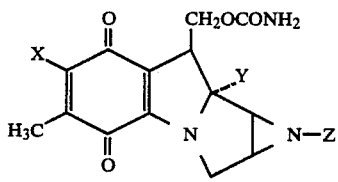

Mitomycins A, B and C are related to one another as set forth in Table 1 below, the designations X Y and Z being those of formula (I).

TABLE I

| Mitomycin: | X | Y | Z |
|---|---|---|---|
| A | $-OCH_3$ | $-OCH_3$ | $-H$ |
| B | $-OCH_3$ | $-OH$ | $-CH_3$ |
| C | $-NH_2$ | $-OCH_3$ | $-H$ |

Mitomycins are derived from mitosane compounds which, generically have the following skeleton II:

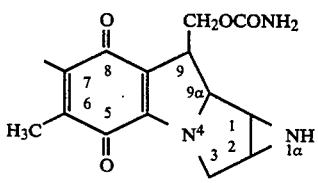

The mitosanes are formed during the cultivation, under artificially controlled conditions, of the microorganism *Streptomyces caespitosus* in a liquid nutrient medium. After separating the resulting mycellium, for example, by filtration, from the obtained culture broth, the various mitomycins may be isolated from the latter by active carbon or preferably non-ion exchange resin adsorption, organic solvent extraction or chromatography on alumina, as disclosed by U.S. Pat. No. 3,660,578 to Hata et al.

The mitosanes are acknowledged as excellent antibiotics but are disadvantageous in that they are toxic to human blood (see U.S. Pat. No. 3,450,705 to Matsui et al.). The relatively highly toxic nature of the compounds has prompted prior art synthesis of numerous mitomycin derivatives and analogues in an attempt to secure compounds having equal or enhanced antibiotic activity but lesser toxicity than the naturally occurring mitomycins.

In the above noted U.S. Pat. No. 3,450,705 to Matsui et al., there are disclosed mitomycin compounds substituted at the 7 position with amino, lower alkyl amino, phenyl amino, or pyridyl, and substituted at the 1a position with haloalkanoyl, halobenzoyl, nitrobenzoyl, alkenoyl, acetyl glycyl, sorbyl or acetyl methionyl.

U.S. Pat. No. 3,558,651 to Matsui et al. discloses mitosane derivatives which are 1a-acyl-7-acyloxy-9a-methoxy compounds.

Certain mitomycins and mitomycin derivatives possess a degree of in vivo anti-tumor activity as well, as reported by Oboshi et al., *GANN*, 58: 315–321 (1967); Usubuchi et al., *GANN*, 58: 307–313 (1967); Matsui et al., *J. Antibiotics*, XXI, No. 3: 189–198 (1968); Japanese Patent No. 68 06 627 to Mastui et al. (as reported in *Chem. Abstracts*, Vol. 69, 86986K (1968)); and Cheng et al., *J. Med. Chem.*, 20, No. 6: 767–770 (1977)

As disclosed in *Mitomycin C: Current Status and New Developments*, Carter et al., Eds., Academic Press, New York (1979), while mitomycin C is active against a relatively broad spectrum of experimental tumors, clinical practice restricts its use to certain carcinomas owing to its toxicity and particularly its myelosuppressive effects.

Recent pre-clinical and clinical studies of mitomycin C have confirmed its activity in a variety of murine and human neoplasms, but its clinical use has been limited by the severe, delayed bone marrow toxicity of the compound, and its narrow therapeutic index (Goldin, A. et al., *NCI-EORTC Symposium on Mitomycin C*, Brussels, Belgium, 1981). In that same reference, Goldin et al. reported preclinical studies which indicated that animal studies are predictive for the clinical toxicities of mitomycin C. In mice, rats, cats, dogs, and rhesus monkeys, the toxicities caused severe bone marrow depression and gastrointestinal damage, and were delayed in onset.

Trials initiated at the Lombardi Cancer Research Center of Georgetown University (Schein, P. S. et al., "Mitomycin C: Current Status and New Developments, pp. 133–143, Carter et al., Eds., Academic Press, New York (1979)) demonstrated that a combination of three drugs, 5-fluorouracil, adriamycin, and mitomycin C, was effective in the treatment of patients with advanced gastric and colorectal cancer. The regimen incorporated mitomycin C administration in a single dose schedule every two months, to decrease the treatment-limiting delayed myelosuppressive effects of the compound.

As disclosed by Remers, U.S. Pat. No. 4,268,676, numerous semi-synthetic analogues of mitomycin C have been prepared in the hope of obtaining compounds with improved therapeutic properties, especially anti-tumor properties. These analogues have involved substitution on the aziridine ring, carbamoyl, or acyl group substitution on the hydroxymethyl side chain, and replacement of the 7-substituent in the quinone ring with other functional groups, especially substituted amines. However, as disclosed by Remers, none of these analogues has emerged as a clinical agent, with the possible exception of the 7-hydroxy analogue of mitomycin C, which has been involved in a recent study in Japan. This analogue is asserted to be less leukopenic than mitomycin C, although it is also much less potent. Further mentioned by Remers are totally synthetic mitomycin analogues of the mitosane type (Mott et al., *J. Med. Chem.*, 21: 493 (1978)), prepared mainly for their antibacterial activity.

Kinoshita, S. et al., *J. Med. Chem.*, 14, No. 2: 103–112 (1971), reported the results of studies of several derivatives of mitomycin substituted in the 1a, 7, and 9a positions. Included in this study were compounds substituted at the 1a position with sulfonyl, ortho-substituted benzoyl, and acyl derivatives.

Iyengar, B. et al., *J. Med. Chem.*, 26: 16–20 (1983), describe a study wherein a series of 7-substituted mitomycin C's and porfiromycins were prepared and screened in standard anti-tumor systems. Certain of the analogues showed better activity than mitomycin C against various tumors, with some less leukopenic and some more leukopenic than the mitomycin C. The authors describe the selection of the 7 position for substitution with the 2-substituted-ethyl analogues because position 7 controls the reduction of the quinone ring, thereby offering an opportunity to gain selectivity between normal cells and certain cancer cells.

Suami, S. et al., *J. Med. Chem.*, 27: 701–708 (1984), prepared a series of 30 different phenyl-substituted mitomycin C analogues, the phenyl substitution being at the 7 position. Seven of the compounds prepared were disclosed as clearly superior to mitomycin C in activity against P-388 murine leukemia.

It is also known from Suami T. et al., *J. Med. Chem.*, 22, No. 3: 247–250 (1979), that N-(2-chloroethyl)-N-nitrosocarbamoyl derivatives of glycosylamines, including three disaccharide derivatives, exhibited strong anti-tumor activity against Leukemia 1210 in mice. Further, it has been demonstrated that glucopyranose derivatives of N-nitrosoureas possess immunogenic and marrow sparing properties (Anderson et al., *Cancer Research* 35, 761–765 (March 1975); Panasci, et al., *J. Clin. Invest.*, Vol. 64, 1103–1111 (October 1979)).

Thus, as may be seen from the above disclosures, research has continued in an effort to synthesize and isolate analogues of the mitomycins which have comparable anti-neoplastic capability, but, at the same time, are less toxic to the animal system than the parent compound.

SUMMARY OF THE INVENTION

Recognizing the long-standing need in the medical and scientific community for compounds demonstrating the anti-neoplastic capability of the mitomycins which would, at the same time, be substantially less toxic to the animal system, the inventors have synthesized mitomycin analogues, said analogues combining glycosidic residues and thiourea moieties.

This effort has resulted in the synthesis of compounds having the following general formula (III):

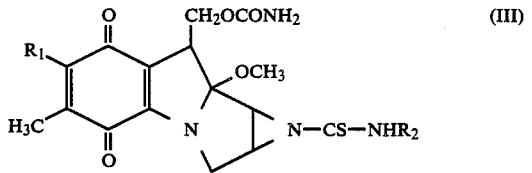

where
$R_1$ is selected from the group consisting of $NH_2$, $C_1$–$C_4$ alkoxy, and a glycosyl residue; and
$R_2$ is selected from hydrogen, $C_1$–$C_4$ alkyl, and a glycosyl residue, with the proviso that either $R_1$ or $R_2$, but not both, contains a glycosyl group. The compounds represened by formula (III) demonstrate the excellent anti-neoplastic capability of the mitomycins and, at the same time, possess reduced bone marrow toxicity and lower overall toxicity.

DESCRIPTION OF THE PREFERRED EMBODIMENTS

Figure 1:
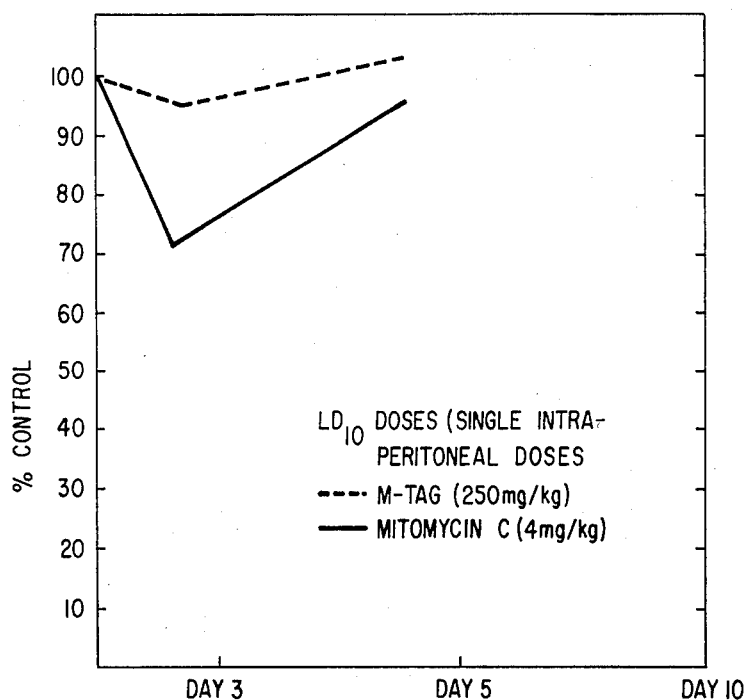
FIG. 1 presents the results of the peripheral leukocyte (WBC) study of Example 10 below.

The 1a- and 7-substituted derivatives of mitomycin of this invention have the general formula (III):

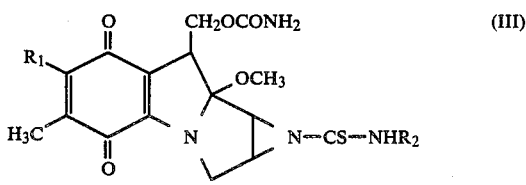

In this formula, $R_1$ is selected from the group consisting of $NH_2$, $C_1$–$C_4$ alkoxy, and a glycosyl residue, and $R_2$ is selected from the group consisting of hydrogen, $C_1$–$C_4$ alkyl, and a glycosyl residue. However, the compounds are characterized in that at least one, but not both of $R_1$ and $R_2$ simultaneously is said glycosyl residue.

By the term "glycosyl residue" is meant monosaccharides and disaccharides and the glycosides and aminated derivatives thereof.

Typical monosaccharides include glucose, galactose, mannose, arabinose, xylose, fructose, ribose, and apiose. Typical disaccharides include sucrose, cellobiose, maltose, lactose, trehalose, gentiobiose, and melibiose.

The glycosides of the mono- and disaccharides may be acylated, partially or completely, with a group $R_3$—CO— where $R_3$ is $C_1$–$C_4$ alkyl. Preferably, the glycosides are acylated with acetyl or propionyl groups.

The glycosyl residues may be in ring configuration as well. Typical six-membered ring compounds, the pyranosyl derivatives, include, but are not limited to, glucopyranose, galactopyranose, mannopyranose, and xylopyranose, as well as the fully or partially acylated derivatives thereof, and further including aminated derivatives thereof.

Typical five-membered ring compounds, furanosyl derivatives, include fructofuranose, arabinofuranose, and xylofuranose, including as well the fully or partially acylated derivatives thereof, and further including aminated derivatives thereof.

Preferred aminated glycosyl residues include those pyranosyl and furanosyl residues which include a 2-acetamido group. Typical of these preferred glycosyl residues are 2-acetamido-3,4,6-tri-0-acetyl-2-deoxy-D-galactopyranosyl; 2-acetamido-3,4,6-tri-0-acetyl-2-deoxy-glucopyranosyl; and 2-acetamido-3,4,5-tri-0-acetyl-2-deoxy-D-xylopryanosyl.

Other preferred glycosyl residues include xylopyranosyl, cellobiosyl, maltosyl, lactosyl, galactopyranosyl, glucopyransyl and glucofuranosyl.

Among the more preferred compounds corresponding to the general formula III above are those set forth in Table II below, where $R_1$ and $R_2$ are as designated therein.

TABLE 2

| Compound | $R_1$ | $R_2$ |
|---|---|---|
| 1 | $NH_2$ | 2-acetamido-3,4,6-tri-0-acetyl-2-deoxy-D-glucopyranosyl |
| 2 | MeO | 2-acetamido-3,4,6-tri-0-acetyl-2-deoxy-D-glucopyranosyl |
| 3 | 2-acetamido-3,4,6-tri-0-acetyl-2-deoxy-D-glucopyranosyl-amine | Ethyl |
| 4 | $NH_2$ | 2-acetamido-3,4,6-tri-0-acetyl-2-deoxy-D-galactopyranosyl |
| 5 | $NH_2$ | 2-acetamido-2-deoxy-D-glucopyranosyl |
| 6 | $NH_2$ | 2-acetamido-2-deoxy-D-galactopyranosyl |
| 7 | $NH_2$ | xylopyranosyl- |
| 8 | $NH_2$ | 3,4,5-tri-0-acetyl-D-xylopyranosyl |
| 9 | $NH_2$ | cellobiosyl |
| 10 | $NH_2$ | maltosyl |
| 11 | $NH_2$ | lactosyl |
| 12 | $NH_2$ | galactopyranosyl |
| 13 | $NH_2$ | glucopyranosyl |
| 14 | $NH_2$ | glucofuranosyl |
| 15 | xylopyranosylamine-3,4,5-tri-0-acetyl | —(NH) |

The synthetic preparation of the mitomycin derivatives of the invention have, as their starting point, mitomycin C. Mitomycin C may be prepared according to the methods generally disclosed in Cheng et al., *J. Med. Chem.*, 20, No. 6: 767-770 (1977). Alternatively, mitomycin C may be obtained from mitomycin A by treatment of mitomycin A with a methanolic-ammonia solution as described by Matsui, M. et al., *J. Antibiotics*, XXI, No. 3: 189 (1968).

To obtain amination of the 7 position, mitomycin C is reacted with a basic methanol solution to produce the sodium salt thereof. Extraction with methanol and precipitation with ether yields the 7-hydroxy-9a-methoxymitosane. Reaction with diazomethane in ether produces, as an intermediate, mitomycin A. Mitomycin A may then be reacted with an excess of the corresponding amine in anhydrous methanol to produce 7-amino-mitomycin C, compound C in FIG. 2. The preparation of mitomycin A from mitomycin C is described more fully in Example 1 below. The preparation of the 7-amino-mitomycin C is described more fully in Example 2 below.

Preparation of derivatives of the mitosanes (mitomycin A A and mitomycin C) substituted at the 1a position with the thiocarbamyl glycose proceeds through the formation of glycosamine-1-isothiocyanate intermediates. These intermediates are prepared by reacting the glycosyl halide, under appropriate conditions, with a metal isothiocyanate. A typical reaction is described more fully in Example 3 below.

The isothiocyanate intermediate is then reacted with the desired mitosane, a typical reaction described more fully in Example 4 below.

Therapeutic methods of the invention comprise the administration of effective amounts of one or more of the compounds of formula (III), as an active ingredient, together with desired pharmaceutically acceptable diluents, adjuvants and carriers, to an animal for antibiotic and/or anti-neoplastic purposes.

As an antibiotic, the compounds of the present invention are useful against all microorganisms susceptible to the anti-bacterial action of the parent compounds, these microorganisms including, but not limited to, Pseudomonas, Staphylococcus, Sarcinia, Diplococcus, Streptococcus, Corynebacterium, Hemophilus, Escherichia, Klebsiella, Proteus, Salmonella, Shigella, Brucella, Mycobacterium, Nocardia, Saccharomyces, Candida, Penicillium, and Aspergillus. Specific microorganism treatable with the compounds of the present invention include *Pseudomonas aeruginosa, Staphylococcus aureus, Staphylococcus albus, Staphylococcus citreus, Sarcina lutea, Diplococcus pneumoniae, Streptococcus hemolyticus, Streptococcus lactis, Corynebacterium diphtheriae, Hemophilus pertussis, Escherichia coli, Klebsiella pneumoniae, Proteus vulgaris, Salmonella typhosa, Salmonella paratyphi, Shigella dysenteriae, Brucella abortus, Brucella megatherium, Brucella mycoides, Brucella anthracius, Mycobacterium ATCC 607, Mycobacterium avium, Mycobacterium phlei, Nocardia asteroides, Saccharomyces cervisiae, Candida albicans, Penicillium glacum, and Aspergillus niger.*

The mitosane derivatives of the present invention are useful in vitro as antiseptics, i.e. for disinfecting. The compounds are also useful topically and internally as a therapeutic agents in combating pathogenic bacteria, e.g. in cases of staphylodermatitis, bacterial pneumoniae, leptopserosis, rickettsiosis, salmonellosis, and the like.

Typically, as a topographical application, the mitosanes of this invention are applied in compositions which deliver the active ingredient in compositions in the range of 0.004 to 4,000 ug/ml As antineoplastic agents, the compounds of the present invention are useful in treating a variety of cancers, including, but not limited to, those cancers susceptible to cell growth suppresion by the parent compounds. Treatment of cancers with the parent compound are described in the following references:

Driscoll, J. S. Hazard G. F. Wood, H. B. Jr., et al., Cancer Chemotherapy Rep., 4, 1, (1974).

Kojima, R., Goldin, A. & Mantel, N., Cancer Chemotherapy Rep., 3, 111 (1972).

Sugiura, K., Cancer Res., 19 (#VIII) 438 (1959).

Oboshi, S., Matsui, M., Ishii, S., et al., GANN, 58, 315 (1967).

Sugiura, K., Cancer Chemotherapy Rep., 13, 51 (1961).

Venditti, J. M., Goldin, A., Miller, I., et al., *Advances in Cancer Chemotherapy*, pp. 201-209 (1978) Editors: H. Umezawa et al., Japan Soc. Press, Tokyo/Univ. Park Press, Baltimore.

Usubuchi, I., Sobajima, Y. Hongo, T., et al., GANN, 58, 307 (1967).

Typical cancers treated by the mitosane derivatives of this invention include, but are not limited to gastric and pancreatic neoplasms (Schein, P.S. et al., "Mitomycin C: Current Status and New Developments, pp. 133–143 & Carter et al. Eds., Academic Press, New York (1979)). Other cancers that may be treated by the invention thereof include lung, breast, anal, colorectal, head & neck & melanoma.

These analogs may also be active against the following tumor systems: Leukemia L-1210, Leukemia P388, P1534 leukemia, Friend Virus Leukemia, Leukemia L4946, Mecca lymphosarcoma, Gardner lymphosarcoma, Ridgway Osteogenic sarcoma, Sarcoma 180 (ascites), Wagner osteogenic sarcoma, Sarcoma T241, Lewis lung carcinoma, Carcinoma 755, CD8F, Mammary carcinoma, Colon 38, Carcinoma 1025, Ehrlich carcinoma (ascites & solid), Krubs 2 carcinoma (ascites), Bashford carcinoma 63, Adenocarcinoma E 0771, B16 Melanoma, Harding-Passey melanoma, Giloma 26, Miyona adenocarcinoma, Walker carcinosarcoma 256, Flexner-Jobling carcinoma, Jensen sarcoma Iglesias sarcoma, Iglesias ovarian tumor, Murphy-Sturn lymphosarcoma, Yoshida sarcoma, Dunning leukemia Rous chicken sarcoma, and Crabb hamster sarcoma.

The compounds of this invention may be administered by any means that effects palliating conditions in warm-blooded animals. For example, administration may be parenterally, i.e., subcutaneously, intravenously, intramuscularly, or intraperitoneally. Parenteral compositions suitable for the practice of the present invention include the active mitosane derivatives as described above, in combination with a pharmacologically acceptable carrier, solvent or diluent. Typical vehicles for parenteral administration of the active ingredient include aqueous vehicles, water-miscible vehicles such as ethyl alcohol, polyethylene glycol, and polypropylene glycol, and nonaqueous vehicles such as corn oil, cotton seed oil, peanut oil, sesame oil, ethyl oleate, isopropyl myristate and benzyl benzoate. Typical parenteral preparations are described by Remington's Pharmaceutical Sciences, Mack Publishing Company, Easton, Pa., 16th Edition, Chapter 84 (1980).

Alternatively, or concurrently, administration can be by the oral route with the active mitosane derivatives being compounded wih pharmacologically acceptable carriers and extenders known to the art.

The dosage administered will be dependent upon the age, health and weight of the recipient, kind of concurrent treatment, if any, frequency of treatment, and the nature of the effect desired.

Therapeutic methods of the present invention comprehend the administration of effective amounts of one or more of the compounds of Formula III as an active ingredient together with desired pharmaceutically acceptable diluents, adjuvants, and carriers, to an animal suffering from a neoplastic disease state. Unit dosage forms of compounds administered according to the methods of the invention may range from about 0.001 to about 5.0 mg and preferably from about 0.004 to about 1.0 mg, of the compounds. Such unit dosage quantities may be given to provide a daily dosage of from about 0.1 to about 100 mg per kg, and preferably from about 0.2 to about 60 mg per kg, of body weight of the animal treated. Parenteral administration, and especially intraperitoneal administration, is the preferred route for antineplastic therapy.

The compounds can be employed in unit dosage form such as tablets, capsules, powder packets, or liquid solutions, suspension, or elixirs, for oral administration, or sterile liquid for formulations such as solutions or suspensions for parenteral use. In such compositions, the active ingredient will ordinarily always be present in an amount of at least 0.5% by weight based on the total weight of the composition and not more than 90% by weight.

Having generally described the invention, a more complete understanding may be obtained by reference to certain examples, which are included for purposes of illustration only and are not intended to be limiting unless otherwise specified.

EXAMPLE 1

Figure 2:
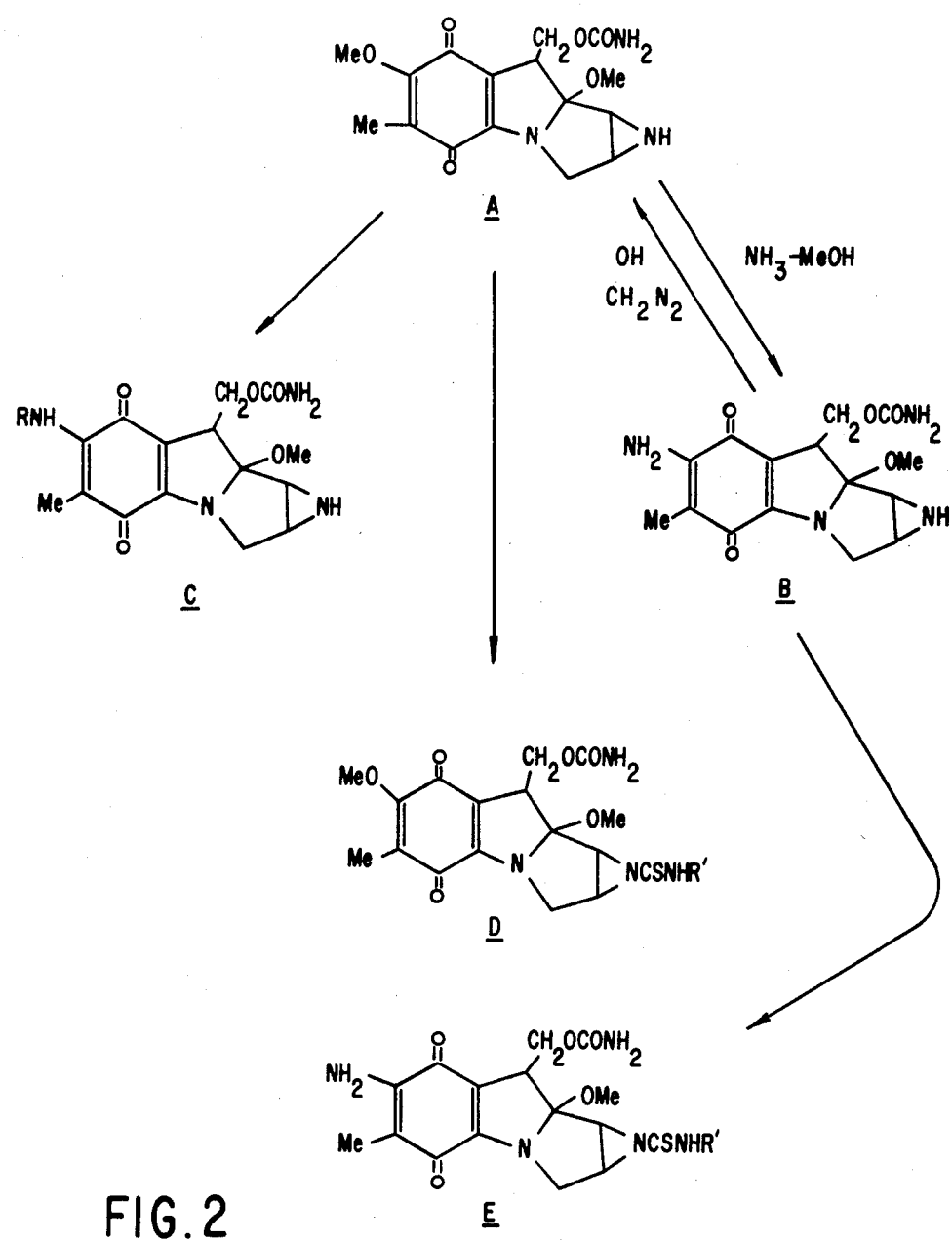
FIG. 2 is a schematic of the synthetic procedures for production of the mitosane compounds of the present invention.

Preparation of Mitomycin A (Compound A of FIG. 2)

1600 mg of mitomycin C were dissolved in 12 ml of 0.1N NaOH solution of 50% methanol with stirring at room temperature for 48 hours. The reaction mixture was quenched with excess dry ice to neutralize the NaOH. This mixture was freeze-dried in vacuo to give the sodium salt plus $NaHCO_3$. A small amount of methanol was added to extract the mitosane compound. The methanol solution was concentrated in vacuo to dryness and the extraction and filtration in methanol was repeated. This methanol extract was precipitated with ether to yield approximately 1400 mg of a blue-purplish powder. This powder was dissolved in methanol and added to a silica gel column (pretreated with acid) and eluted with methanol. The methanol was evaporated in vacuo to dryness to give 1200 mg of a reddish-purple compound, 7-hydroxy-9a-methoxymitosane. 1000 mg of this precipitate were dissolved in 200 ml of ethyl acetate and cooled to 5° C.; and diazomethane in ether was added in excess. The mixture was allowed to stand at room temperature for 30-45 minutes. This mixture was then evaporated in vacuo to dryness to give a purplish residue which was then dissolved in ethyl acetate and added to a silica gel column and eluted with ethyl acetate. The reddish-purple band was collected and evaported to dryness in vacuo and recrystallized from ether to give 650 mg of purple needles of mitomycin A with a melting point of 159°-160° C. (160° C. lit.).

TLC (ETOAC:Acetone) one spot $R_f=0.91$; UV (MeOH) 216 and 358 mu $NMR(CDCl_3)$; appearance of singlet at 4.04 corresponding to the 7-methoxy group which is not present in the parent compound mitomycin C.

EXAMPLE 2

Preparation of 7-Amino-Mitomycin (Compound C of FIG. 2)

Mitomycin A, 500 mg, was dissolved in 10 ml of MeOH (anhydrous) and an excess of the corresponding amine was added with stirring under a nitrogen atmosphere at room atmosphere for 24 hours. The course of reaction was followed with TLC ($ETOAc:Me_2CO$, 1:1). The reaction mixture was evaporated to dryness in vacuo at room temperature and the crude residue redissolved in a minimal amount of MeOH; a purplish powder was precipitated with addition of petroleum ether. The powder was filtered, collected, and dried in vacuo over $P_2O_5$. The dried powder was recrystallized from ethyl acetate. NMR analysis showed no singlet at 4.04. See Matsui, M. et al., *J. Antibiotics*, XXI, No. 3: 189 (1968).

EXAMPLE 3

Figure 3:
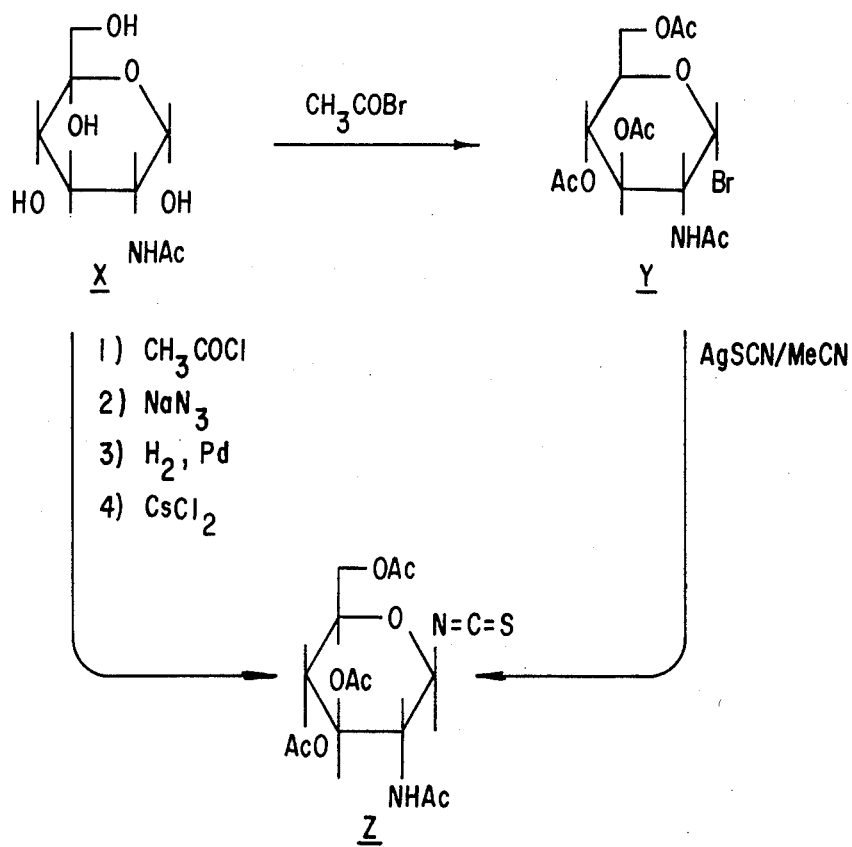
FIG. 3 is a schematic of the synthetic procedure for preparation of isothiocyanate intermediates useful in the preparation of the mitosane derivatives of this invention.

Preparation of the Glycosyl Isothiocyanate Intermediate 2-acetamido-2-deoxy-D-glucopyranose (Compound X of FIG. 3), 10 grams, was mixed with 22 ml of acetyl bromide with cooling and allowed to react at room temperature under nitrogen atmosphere for 16 hours and worked up as follows: 100 ml of methylene chloride was added to the reaction mixture and the mixture poured onto 100 grams of crushed ice with 20 ml of water. The organic layer was separated and dried over anhydrous magnesium sulfate. The $CH_2Cl_2$ was evaporated in vacuo to 10–15 ml, glacial acetic acid added, and the mixture chilled to give 8–8.5 g (47%) mp 180°–190° C., $[\alpha]_D + 148$ (Cl,CHCl$_3$). The migrated product had a mp of 180°–200° C. decomp. $[\alpha]_D^{20} + 118$, (Cl, HOAc) (Compound Y of FIG. 3).

1000 mg of this bromo compound, Y intermediate, was dissolved in 25 ml of freshly distilled acetonitrile (from $P_2O_5$) along with 1000 mg of silver isothiocyanate (protected from light) and heated to 50°–60° C. for approximately ½ hour. This mixture was cooled and evaporated in vacuo (@40° C. water bath). Recrystalliztion of the residue from EtOAc gave 915–920 mg (94–98%) $[\alpha]_D^{20} + 9$ (Cl, CHCl$_3$). This was compound Z. NMR(CDCl$_3$): 5.7 δ J=8.5–9 Hz doublet (β anomer H-1); 2.0–2.116 δ (NAc, 3,4,6 tri-O-acetyl protons). This compound Z showed one spot on TLC (EtOAc:MeOH; 5:1) R$_f$ 0.94) developed with NH$_4$SO$_4$H$_2$SO$_4$ spray and charring: IR (EtOAc); 2020 cm$^{-1}$ (N=C=S). This compound was 2-acetamido-3,4,6,-tri-O-acetyl-2-deoxy-B-D-glucosamine-1-isothiocyanate (Compound Z of FIG. 3).

EXAMPLE 4

Preparation of 1a(N-2-acetamido-3,4,6-tri-O-acetyl-2-deoxy-D-glucopyranosylthiocarbamoyl)-mitomycin C (M-TAG)

Now compound Z was coupled with mitomycin C in freshly distilled tetrahydrofuran (THF) (distilled from P$_2$O$_5$ under N$_2$): 200 mg of mitomycin C and 240 mg of compound Z in 200 ml of dry THF were stirred at room temperature under N$_2$ atmosphere for 24 hours. The reaction was followed with TLC (silica gel; EtOAc:-Me$_2$CO; 1:1); R$_f$=0.80, one spot. NMR(DMSO-d$_6$) δ: disappearance of aziridine NH moiety at 2.6δ; addition of multiplet (1.988–2.02 δ corresponding to compound Z's OAc's to the mitomycin C basic NMR chemical shift. Also a doublet at 5.7δ, J=8–9 Hz (β anomer of compound Z). IR(EOTAc); no band for N=C=S at 2020 cm$^{-1}$. Theoretical analysis for $C_{30}H_{38}N_6O_{13}S$; C=49.85; H=5.31; N=11.63 S=4.44: Found; C=49.43; H=5.57; N=11.06; S=4.49, confirming M-TAG.

ANTIBIOTIC STUDIES

EXAMPLE 5

The antibiotic characteristics of 1a-(N-2-acetamido-3,4,6-tri-O-acetyl-2-deoxy-D-glucopyranosylthiocarbamoyl)-mitomycin C were evaluated against seven microorganisms and compared with mitomycin C as well.

Bacteria were grown in a standard growth culture at pH 7.2. After the cultures were incubated at 37° C. overnight and diluted into fresh medium, controls and the test antibiotics dissolved in 0.3% hydroxy propylcellulose (HPC) were added at various concentrations and then reincubated overnight. The measure of antibiotic activity was determined by the amount of bacterial growth inhibition as shown by measurement of the optical density at 660 nm. The results are shown in Table 3 below.

As may be seen from Table 3, the mitomycin C derivative demonstrates excellent antibiotic activity, possessing anti-bacterial activity against gram positive and gram negative microorganisms in a fashion similar to that of the naturally occurring mitomycins. Further, the mitomycin-C derivatives are less toxic on a log dose-response scale when compared to the parent mitomycin-C.

TABLE 3

| | CONCENTRATION (mcg/ml) 1a-(N—2 acetamido-3,4,6-tri-O—acetyl-2-deoxy-D-glucopyranosyl thio carbamoyl)-mitomycin C | | | | |
|---|---|---|---|---|---|
| Name of Microorganism | 400 | 40 | 4.0 | 0.4 | 0.04 |
| W3100 (*E. coli*) | 92 (0.04)* | 86 (0.07) | 50 (0.30) | 31 (0.51) | 33 (0.48) |
| Pseudomonas Sp. | 78 (0.11) | 75 (0.11) | 75 (0.13) | 45 (0.35) | 30 (0.52) |
| TA100 (Salmonella Sp.) | 95 (0.02) | 80 (0.97) | 80 (0.97) | 78 (0.11) | 46 (0.34) |
| Staphylococcus Sp. | 100 (0.00) | 94 (0.03) | 96 (0.018) | 95 (0.02) | 30 (0.52) |
| *Klebsiella Pneumonia* | 92 (0.04) | 40 (0.40) | 26 (0.59) | 24 (0.62) | 22 (0.66) |
| Listeria Sp. | 100 (0.00) | 92 (0.036) | 26 (0.59) | 26 (0.59) | 26 (0.59) |
| WP$_{2s}$ (*E. coli*) | 98 (0.009) | 76 (0.12) | 50 (0.30) | 51 (0.29) | 39 (0.41) |
| | COMPOUND B: MITOMYCIN C: | | | | |
| W3100 (*E. coli*) | 800 (0.097) | 80 (0.097) | 88 (0.06) | 89 (0.051) | 74 (0.13) |
| Pseudomonas Sp. | 71 (0.15) | 72 (0.14) | 78 (0.11) | 78 (0.11) | 78 (0.11) |
| TA100 | 80 (0.97) | 81 (0.092) | 85 (0.07) | 84 (0.076) | 84 (0.076) |
| Staphylococcus Sp. | 90 (0.046) | 91 (0.041) | 93 (0.03) | 93 (0.03) | 30 (0.52) |
| *Klebsiella Pneumonia* | 75 (0.13) | 85 (0.07) | 87 (0.06) | 82 (0.086) | 30 (0.52) |
| Listeria Sp. | 96 (0.018) | 96 (0.018) | 93 (0.03) | 95 (0.13) | 85 (0.07) |
| WP$_{2s}$ | 85 (0.07) | 85 (0.07) | 84 (0.076) | 86 (0.07) | 70 (0.16) |
| | CONTROLS: | | | | |
| W3100 (*E. coli*) | 45 | 37 | 36 | 36 | 36 |
| Pseudomonas Sp. | 35 | 31 | 33 | 35 | 35 |
| TA100 | 31 | 36 | 36 | 36 | 46 |
| Staphylococcus Sp. | 37 | 38 | 32 | 39 | 24 |
| *Klebsiella Pneumonia* | 39 | 30 | 31 | 30 | 30 |
| Listeria Sp. | 38 | 27 | 36 | 36 | — |
| WP$_{2s}$ | 48 | 47 | 32 | 35 | 32 |

ANIMAL STUDIES

EXAMPLE 6

Determination of Toxic Doses of the Compound in Normal Mice

Normal CD2F$_1$ male mice, 6–10 weeks old, were used for initial studies to determine toxic single doses of the thiocarbamyl N-Ac glucopyranosyl derivative of mitomycin C, designated M-TAG, in mice (Table 4 below). Doses of the compound in the range of the $LD_{10}$ dose (single intraperitoneal dose that produces toxic deaths in 10% of the normal mice) were then tested for antitumor activity against several murine tumor systems (Examples 7, 8 and 9 below). The $LD_{10}$ dose was then evaluated in normal $CD2F_1$ mice for effects on the hematopoietic system (Example 10 below).

Normal $CD2F_1$ male mice were used to determine the $LD_{10}$ dose (single intraperitoneal dose toxic to 10% of normal mice) for the compound. Various concentrations of the compound were prepared immediately prior to use by dissolving the drug in absolute ethanol, and then adding the resultant solution to either sterile water or hydroxypropyl cellulose (HPC, 0.3% in saline) at a final concentration of 8% ethanol and 92% water or HPC vehicle. Drug was administered intraperitoneally (i.p.) in a volume of 0.1 ml per 10 grams body weight. The normal mice were then observed for up to 45 days post-drug administration to determine deaths due to acute and chronic (up to 45 days) drug toxicity.

Results are summarized in the following Table 4:

TABLE 4

| Dose (mg/kg) | Deaths due to drug toxicity |
|---|---|
| 250 | 0/10 |
| 275 | 1/10 $LD_{10}$ |
| 300 | 3/10 |

The approximate $LD_1$ dose of the compound (single i.p. dose toxic to 10% of normal mice) was 250-275 mg/kg; single doses in this range were used to evaluate antitumor activity in three murine tumor systems.

EXAMPLE 7

Determination of Murine P338 Leukemia Antitumor Activity

The murine P388 leukemia system, maintained intraperitoneally in female DBA/2 mice, was used to evaluate antitumor activity. This tumor was selected because of its known sensitivity to the parent compound, mitomycin C (Driscoll et al., *Cancer Chemotheraphy Reports*, 4: 1 (1974)). The compound (M-TAG) and the parent mitomycin C were both dissolved in absolute ethanol, and the resultant solution was added to either sterile water or HPC vehicle to result in a final concentration of 8% ethanol-92% sterile water or HPC vehicle.

The compound (M-TAG) and mitomycin C were administered to groups of 10 $CD2F_1$ male mice on day one after implantation of $1 \times 10^6$ P388 leukemia cells i.p. (in a volume of 0.10 ml). The P388 antileukemic activity of the test compound (M-TAG) was assessed by mean survival days, percentage increased life span or %ILS, and number of survivors after 45 days. The %ILS was calculated as follows:

%ILS=(T-C)/C×100 where T is the mean survival days of the treated mice and C is the mean survival days of the untreated mice P388 antileukemic activity of M-TAG was compared to that achieved with the clinically used mitomycin C, and the results are summarized in the following Table 5:

TABLE 5

| Antitumor Activity against P388 Leukemia | | | |
|---|---|---|---|
| Drug | Dose (mg/kg) | % ILS | Mean Survival (Days) |
| M-TAG | 250 mg/kg[a] (346 μmol/kg) | 85% | 22 |
| Mitomycin C | 4 mg/kg[a] (12 μmol/kg) | 84% | 21 |

[a]approximate $LD_{10}$ dose

There was no statistical difference in the overall survivals when an $LD_{10}$ dose of M-TAG was compared to an $LD_{10}$ dose of mitomycin C.

EXAMPLE 8

Determination of Murine Ehrlich Ascites Antitumor Activity

The antitumor activity of M-TAG for the murine Ehrlich ascities tumor was also determined. Ehrlich ascites was maintained i.p. in female BALB/C mice. For antitumor studies, $1 \times 10^7$ Ehrlich ascites cells (in 0.10 ml) were implanted i.p. in male $BD2F_1$ mice. Drug was administered i.p. (single $LD_{10}$ dose) one day after tumor implantation. The %ILS was calculated as previously described, and the results are presented in the following Table 6:

TABLE 6

| Antitumor Activity against Ehrlich Ascites | | | |
|---|---|---|---|
| Drug | Dose (mg/kg) | % ILS | Mean Survival (Days) |
| M-TAG | 250 mg/kg[a] | 66% | 22.8 |
| Mitomycin C | 4 mg/kg[a] | 82%[b] | |

[a]approximate $LD_{10}$ dose
[b]50% of the mice were alive on Day 30

EXAMPLE 9

Determination of Murine B16 Melanoma Antitumor Activity

Activity against the murine B16 melanoma is currently being determined. The tumor is maintained subcutaneously in female C57 mice, and antitumor activity is determined in male $BD2F_1$ mice that have received 0.5 ml of a 10% tumor brei i.p., with drug administered i.p. on day 1 following tumor implantation. All mice which received M-TAG (250 mg/kg) or mitomycin C (4 mg/kg) were alive on day 10, after all vehicle-control mice died. On day 20, 6 out of 10 mice receiving M-TAG and 5 out of 10 mice receiving mitomycin C were alive.

In summary, the new analogue (M-TAG) has antitumor activity against the murine P388 leukemia equivalent to that achieved with the parent mitomycin C. M-TAG also demonstrated significant antitumor activity against the murine Ehrlich ascites and B16 melanoma tumors.

EXAMPLE 10

Determination of the Effects of the Compound on the Hematopoietic System in Mice Effects on Peripheral Leukocyte Count Measurement of peripheral leukocyte (WBC) count was performed using a 20-ul sample of retro-orbital sinus blood obtained from normal $CD2F_1$ male mice on days 3, 4, 5, 6 and 10 following i.p. administration of doses in the range of the $LD_{10}$; groups of 10 mice were treated with drug as described previously. Comparative studies were performed with M-TAG and mitomycin C. Drug was dissolved in absolute ethanol, and then adjusted to a final concentration of 8% ethanol-92% sterile water. Blood samples obtained were diluted in 9.98 ml of Isoton (a neutral isotonic buffer solution) and counted in a Coulter counter after lysis with Zapoglobin (an enzyme solution which lyses red blood cells but not white blood cells). WBC counts are expressed as a percentage of values from control mice receiving drug vehicle only. Results of the peripheral leukocyte (WBC) study are presented in FIG. 1.

The nadir for mitomycin C (4 mg/kg) occurred on day 3 or 4 after drug administration, and was 76% of the control. In contrast, the compound (M-TAG, 250 mg/kg) produced no significant depression in WBC counts at all days tested (days 3, 4, 5, 6 and 10). These data demonstrate M-TAG to have no significant myelotoxicity as measured by WBC depression, in contrast to the 24% decrease in WBC counts produced by an equivalent $LD_{10}$ dose of mitomycin C. The WBC nadir depression produced by mitomycin C was significantly greater than that produced by an equitoxic dose of M-TAG ($P<0.01$).

EXAMPLE 11

Human CFU-C assay

The human bone marrow CFU-C assay measures human bone marrow cells committed to granulocyte-macrophage differentiation. This in vitro assay serves as a model for predicting the relative toxicity of an experimental drug on the granulocytic series of the bone marrow. The derivative, M-TAG, was tested at an approximate 30-40-fold increased molar concentration relative to the parent mitomycin C. This concentration was increased to correspond to the demonstrated 30-40-fold difference in $LD_{10}$ dose in mice (see Table 5). Both drugs were dissolved in 0.5% DMSO, and nucleated human bone marrow cells were exposed in vitro (for 90 minutes at 37° C.) to varying concentrations of each drug. The cells were then plated in triplicate in 3% agar for the CFU-C assay, using GCT, (Giant Cell Tumor) extract (Gibco, Grand Island, N.Y.) as colony-stimulating factor. (Lohrmann and Schreml "*Cytotoxic Drugs and the Granulopoietic System*", Springer-Verlag Press, (1982)). The following results were obtained:

| Drug Concentration | | CFU-C: % Control |
|---|---|---|
| Mitomycin C- | .01 mM | <10% |
| | .005 mM | 21% |
| | .001 mM | 30% |
| M-TAG | 1.0 mM | <20% |
| | 0.5 mM | 43% |
| | 0.1 mM | 66% |

These data further demonstrate the reduced bone marrow toxicity of M-TAG compared to the parent mitomycin-C.

EXAMPLE 12

The toxicity of the mitosanes (including the derivatives of this inventon) can be evaluated by their induction of lambda prophage development in E. coli WP2s (λ). This short-term bacterial assay for genotoxic effects is used to predict the carcinogenicity of the drugs tested. (T. G. Rossman, et al., Environmental Mutagenesis 6, 59–69 (1984)).

Figure 4:
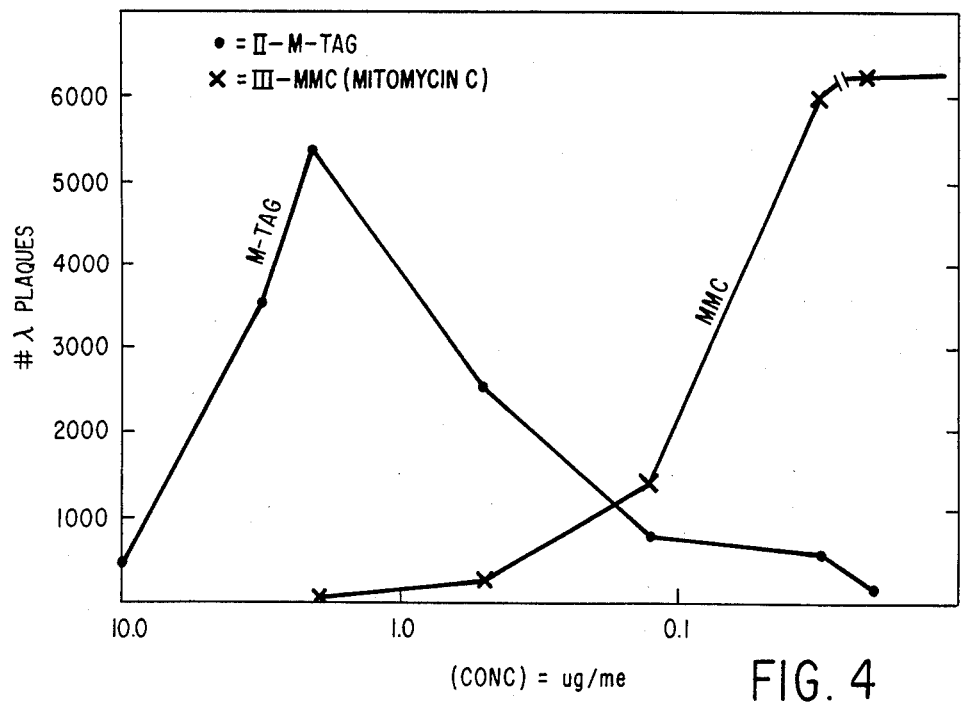
FIG. 4 is a graph comparing induction of phage formation by M-TAG and mitomycin C at various concentrations as a measure of genotoxicity.

In a micro suspension assy for prophage induction in E. coli WP2s (λ), using a 24 hour exposure time and MNNG (N-methyl-N-nitrosoguanidine) as a positive control, the analog of mitomycin C, M-TAG, produced maximum induction of λ-phage at 2 mg/ml, while maximum induction with mitomycin C occurred at 0.02 mg/ml. Each compound produced a maximum 50–100% increase of phage titer over control. Both compounds were genotoxic, but the toxicity of M-TAG was about 50 fold less than the parent compound. (See Table 8 and FIG. 4). Hence M-TAG also demonstrates in this set of experiments that it is as active as the parent compound but much less genotoxic.

Microsuspension Assay

All strains used were derivatives of E. coli B/r. WP2s (λ) is a lysogen or WP2s (trp E, UVrA. SR714 was used as indicator. Cultures were developed in Minimal Broth Davis (Difco) which contains 0.2% glucose and 20 ug/ml of tryptophan (MST). Mid-exponential phase cultures were used for every experiment (O.D. 0.3 at 550 nm).

Two fold dilutions of the test drug in 150 ml MST were made in tissue culture-multiwell plate.

After scoring for growth, an aliquot of 25 ml from each well was diluted in 5 ml MST. Diluted samples were added to tubes containing 2.5 ml of soft agar (0.65% Bacto agar, 10 mM MgSO$_4$) and held at 47° C. A mid-exponential culture of indicator strain was added and tubes mixed and poured onto nutrient broth agar plates (Difco). After overnight incubation at 37° C., the plates were scored for plaques. All assays were run in duplicate.

TABLE 8

Induction of Propage in Microtiter Assay

| | *PFU/DISH | | | |
|---|---|---|---|---|
| [Conc] ug/ml | Control | MMC | MTAG | MNNG[2] |
| 200.000 | 156.0 | — | 14.5 | 473.5 |
| 50.000 | — | — | 169.0 | 2366.0 |
| 12.500 | — | — | 461.5 | — |
| 3.125 | — | 14.0 | 3516.5 | — |
| 2.000 | — | 34.0 | 5395.0 | — |
| 0.500 | 182.0 | 260.0 | 2535.0 | — |
| 0.125 | — | 1449.5 | 799.5 | 416.0 |
| 0.03125 | — | >6000.0[1] | 591.5 | 1813.5 |
| 0.020 | — | >6000.0[1] | 152.5 | — |
| 0.005 | — | >6000.0[1] | 148.5 | — |
| 0.00125 | — | 1228.5 | — | — |
| 0.0003125 | — | 565.5 | — | — |

*PFU (plaque forming units)
Strain WP2$_b$, SR714 indicator used above
[1]Too many to count
[2]MNNG (N—methyl-N'—nitrosoguanidine.
Note: Exposure time to all above chemicals was 24 hours.

In summary, in vivo murine studies demonstrate the compounds of this invention to have significant antibacterial activity against Escherichia, Pseudomonas, Salmonella, Staphylococcus, klebsiella, and Listeria and antitumor activity against the murine P388, Ehrlich ascites and melanoma tumor systems at doses producing no significant bone marrow toxicity, as determined by depression of peripheral leukocyte (WBC) count. Human CFU-C assay results (Example II) further demonstrate the reduced bone marrow toxicity of the compounds of this invention as compared to the parent compounds. Further, studies of prophage induction in E. coli demonstrate that M-TAG is about 50-fold less genotoxic than mitomycin C (Example 12).

Having now fully described this invention, it will be apparent to one of ordinary skill in the art that many changes and modifications can be made thereto without changing the scope or meaning thereof.

What is claimed as new and is desired to be covered by Letters Patent is:

1. A compound having the formula:

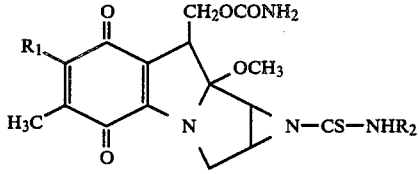

where
R$_1$ is selected from the group consisting of NH$_2$, C$_1$–C$_4$ alkoxy and a glycosyl residue; and
R$_2$ is selected from the group consisting of hydrogen, C$_1$–C$_4$ alkyl, and a glycosyl residue;
with the proviso that at least one but not both R$_1$ and R$_2$ contains a glycosyl residue.

2. The compound of claim 1 wherein R$_1$ is selected from the group consisting of NH$_2$ methoxy, and 3,4,5-tri-O-acetyl-xylopyranosylamine and R$_2$ is selected from the group consisting of 2-acetamido-3,4,6-tri-O-acetyl-2-deoxy-D-glucopyranosyl; 2-acetamido-2-deoxy-D-glucopyranosyl; 2-acetamido-2-deoxy-D-galactopyranosyl; xylopyranosyl; 3,4,5-tri-O-acetyl-D-xylopyranosyl; cellobiosyl; maltosyl; lactosyl; galactopyranosyl; glucopyranosyl; glucofuransoyl; ethyl; and hydrogen.

3. The compound of claim 1 wherein R$_1$ is NH$_2$ and R$_2$ is N-2-acetamido-3,4,6-tri-O-acetyl-2-deoxy-D-glucopyranosyl.

4. A pharmaceutical composition comprising a compound having the formula:

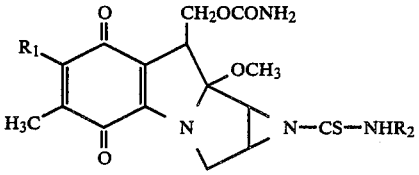

where
R$_1$ is selected from the group consisting of NH$_2$, C$_1$–C$_4$ alkoxy and a glycosyl residue; and
R$_2$ is selected from the group consisting of hydrogen, C$_1$–C$_4$ alkyl, and a glycosyl residue;
with the proviso that at least one but not both R$_1$ and R$_2$ contains a glycosyl residue, together with a pharmaceutically acceptable carrier.

5. The composition of claim 4, wherein R$_1$ is selected from the group consisting of NH$_2$ methoxy, 3,4,5-tri-O-acetyl-xylopyranosylamine and R$_2$ is selected from the group consisting of 2-acetamido-3,4,6-tri-O-acetyl-2-deoxy D-glucopyranosyl; 2-acetamido-2-deoxy-D-glucopyranosyl; 2-acetamido-2-deoxy D-galactopyranosyl; xylopyranosyl; 3,4,5-tri-O-acetyl-D-xylopyranosyl; cellobiosyl; maltosyl; lactosyl; galactopyranosyl; glucopyranosyl; glucofuranosyl; ethyl; and hydrogen.

6. The composition of claim 4 wherein R$_1$ is NH$_2$ and R$_2$ is N-2-acetamido-3,4,6-tri-O-acetyl-2-deoxy-D-glucopyranosyl.

7. A method of suppressing bacterial growth comprising contacting said bacteria, in an antibacterial amount, with a compound having the formula:

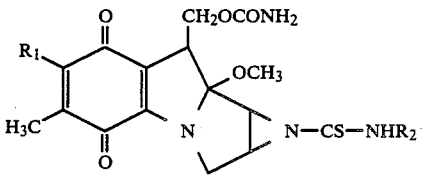

where
R$_1$ is selected from the group consisting of NH$_2$, C$_1$–C$_4$ alkoxy and a glycosyl residue; and
R$_2$ is selected from the group consisting of hydrogen, C$_1$–C$_4$ alkyl, and a glycosyl residue;
with the proviso that at least one but not both R$_1$ and R$_2$ contains a glycosyl residue.

8. The method of claim 7 wherein R$_1$ is selected from the group consisting of NH$_2$, methoxy, and 3,4,5-tri-O-acetyl-xylopyranosylamine and R$_2$ is selected from the group consisting of 2-acetamido-3,4,6-tri-O-acetyl-2-deoxy-D-glycopyranosyl; 2-acetamido-2-deoxy-D-glucopyranosyl; 2-acetamido-2-deoxy D-galactopyranosyl; xylopyranosyl; 3,4,5-tri-O-acetyl-D-xylopyranosyl; cellobiosyl; maltosyl; lactosyl; galactopyranosyl; glucopyranosyl; glucofuranosyl; ethyl; and hydrogen.

9. The method of claim 7 wherein R$_1$ is NH$_2$ and R$_2$ is N-2-acetamido-3,4,6-tri-O-acetyl-2-deoxy-D-glucopyranosyl.

10. The method of claim 7 wherein said bacterial growth comprises bacteria selected from the group consisting of Escherichia, Pseudomonas, Salmonella, Staphylococcus, Klebsiella, and Listeria.

11. A method of suppressing bacterial growth in an animal comprising administering to said animal an antibacterial amount of a compound having the formula:

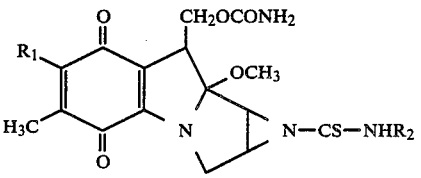

where
R$_1$ is selected from the group consisting of NH$_2$, C$_1$–C$_4$ alkoxy and a glycosyl residue; and
R$_2$ is selected from the group consisting of hydrogen, C$_1$–C$_4$ alkyl, and a glycosyl residue;
with the proviso that at least one but not both R$_1$ and R$_2$ contains a glycosyl residue.

12. A method according to claim 11 wherein R$_1$ is selected from the group consisting of NH$_2$' methoxy, and 3,4,5-tri-O-acetyl-xylopyranosylamine and R$_2$ is selected from the group consisting of 2-acetamido-3,4,6-tri-O-acetyl-2-deoxy-D-glucopyranosyl; 2-acetamido-2-deoxy-D-glucopyranosyl; 2-acetamido-2-deoxy D-galactopyranosyl; xylopyranosyl; 3,4,5-tri-O-acetyl-D-xylopyranosyl; cellobiosyl; maltosyl; lactosyl; galactopyranosyl; glucopyranosyl; glucofuranosyl; ethyl; and hydrogen.

13. A method according to claim 11 wherein R$_1$ is NH$_2$ and R$_2$ is N-2-acetamido-3,4,6-tri-O-acetyl-2-deoxy-D-glucopyranosyl.

14. A method for suppressing growth of cancer cells selected from the group consisting of leukemia cells and melanoma cells susceptible to growth suppression in an animal which comprises administering to said animal, in a growth suppressing amount, a compound having the formula:

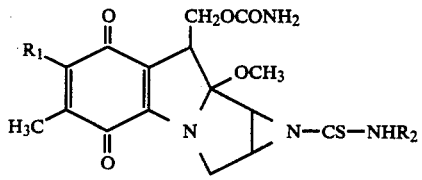

where
$R_1$ is selected from the group consisting of $NH_2$, $C_1$–$C_4$ alkoxy and a glycosyl residue; and
$R_2$ is selected from the group consisting of hydrogen, $C_1$–$C_4$ alkyl, and a glycosyl residue;
with the proviso that at least one but not both $R_1$ and $R_2$ contains a glycosyl residue.

15. The method of claim 14 wherein $R_1$ is selected from the group consisting of $NH_2$, methoxy, and 3,4,5-tri-O-acetyl-xylopyranosylamine and $R_2$ is selected from the group consisting of 2-acetamido-2-deoxy-3,4,6-tri-O-acetyl-D-glucopyranosyl; 2-acetamido-2-deoxy-D-glucopyranosyl; 2-acetamido-2-deoxy-D-galactopyranosyl; xylopyranosyl; 3,4,5-tri-O-acetyl-D-xylopyranosyl; cellobiosyl; maltosyl; lactosyl; galactopyranosyl; glucopyranosyl; glucofuranosyl; ethyl; and hydrogen.

16. The method of claim 14 wherein $R_1$ is $NH_2$ and $R_2$ is N-2-acetamido-3,4,6-tri-O-acetyl-2-deoxy-D-glucopyranosyl.

* * * * *